United States Patent
Hikawa et al.

(10) Patent No.: US 8,551,018 B2
(45) Date of Patent: Oct. 8, 2013

(54) PUNCTURE SET

(75) Inventors: Masami Hikawa, Nakakoma-gun (JP);
Takao Matsuno, Nakakoma-gun (JP);
Hisao Nishikawa, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 314 days.

(21) Appl. No.: 12/681,301

(22) PCT Filed: Aug. 25, 2008

(86) PCT No.: PCT/JP2008/065120
§ 371 (c)(1),
(2), (4) Date: Apr. 1, 2010

(87) PCT Pub. No.: WO2009/044594
PCT Pub. Date: Apr. 9, 2009

(65) Prior Publication Data
US 2010/0249650 A1    Sep. 30, 2010

(30) Foreign Application Priority Data
Oct. 2, 2007  (JP) .................................. 2007-258495

(51) Int. Cl.
*A61B 5/00*    (2006.01)
(52) U.S. Cl.
USPC ........................................................ 600/583
(58) Field of Classification Search
USPC .......................... 600/573, 583; 606/181–183
See application file for complete search history.

(56) References Cited

U.S. PATENT DOCUMENTS

| 5,385,571 A | 1/1995 | Morita |
| 7,452,366 B2 * | 11/2008 | Chen et al. ..................... 606/181 |
| 7,470,238 B2 * | 12/2008 | Sakata et al. .................. 600/583 |
| 2005/0131441 A1 | 6/2005 | Iio et al. |

(Continued)

FOREIGN PATENT DOCUMENTS

| JP | 6-023505 A | 3/1994 |
| JP | 6-114039 A | 4/1994 |

(Continued)

OTHER PUBLICATIONS

International Search Report issued by the Japanese Patent Office on Sep. 16, 2008 as the International Searching Authority in International Application No. PCT/JP2008/065120.

(Continued)

*Primary Examiner* — Max Hindenburg
(74) *Attorney, Agent, or Firm* — Buchanan Ingersoll & Rooney PC

(57) ABSTRACT

A puncture set includes a puncture needle unit and puncture device. The puncture needle unit includes a puncture needle and a tubular casing, with the puncture needle having a needle hub and a needle body possessing a needle point. The tubular casing movably receives the puncture needle and has an opening from which the needle point can project. The puncture device has a housing, an installation section at which the casing is removably installed, and a plunger having a connection section connected to the needle hub in an installed state where the casing is installed on the installation section. Casing-side projections project from the outer periphery of the casing and are circumferentially arranged. Installation section-side projections project from the inner periphery of the installation section and are circumferentially arranged. In the installed state, at least one installation section-side projection is located between adjacent casing-side projections.

12 Claims, 10 Drawing Sheets

(56) References Cited

U.S. PATENT DOCUMENTS

| | | |
|---|---|---|
| 2005/0251188 A1 | 11/2005 | Chen et al. |
| 2007/0293883 A1 | 12/2007 | Horie |
| 2008/0077167 A1* | 3/2008 | Flynn et al. .................. 606/172 |
| 2008/0103517 A1 | 5/2008 | Takemoto et al. |
| 2009/0143810 A1 | 6/2009 | Kitamura et al. |

FOREIGN PATENT DOCUMENTS

| | | |
|---|---|---|
| JP | 2000-245717 A | 9/2000 |
| JP | 2006-255432 A | 9/2006 |
| WO | WO 2006/028096 A1 | 3/2006 |
| WO | WO 2007/037207 A1 | 4/2007 |
| WO | WO 2007/069572 A1 | 6/2007 |

OTHER PUBLICATIONS

Non-English version of Written Opinion issued by the Japanese Patent Office on Sep. 16, 2008 as the International Searching Authority in International Application No. PCT/JP2008/065120.

Extended European Search Report issued on Sep. 7, 2010 by the European Patent Office in corresponding European Patent Application No. 08835126.7.

* cited by examiner

PUNCTURE SET

TECHNICAL FIELD

The present invention relates to a puncture set.

BACKGROUND ART

Due to the rise in the number of diabetic patients in recent years, it is recommended that diabetic patients perform self-monitoring of blood glucose by monitoring daily variations of blood glucose. For measuring blood glucose levels, a blood glucose measuring device for automatically measuring the amount of glucose in blood is used. Prior to measurement, it is necessary for the diabetic patient to sample his or her own blood.

Blood is sampled by puncturing the fingertip with a puncture needle, and thereafter pressing the region around the punctured spot with another finger or fingers to squeeze out the blood. The fingertip is punctured by a puncture set (see, for example, Patent Document 1) comprising a puncture needle unit having a puncture needle and a casing that houses the puncture needle therein, and a puncture device having a mount on which the puncture needle unit is detachably mounted and a plunger that is coupled to the puncture needle while the puncture needle unit is mounted on the mount. More specifically, the puncture needle unit is inserted into the puncture device and mounted in place, and then the puncture device with the puncture needle unit mounted therein is actuated to cause the puncture needle of the puncture needle unit to project and puncture the fingertip. After the puncture needle has punctured the fingertip, i.e., after the puncture needle has been used, the puncture needle unit is removed from the puncture device. The puncture set disclosed in Patent Document 1 is arranged to have a clearance (gap) between the casing of the puncture needle unit and the mount of the puncture device, for thereby allowing the puncture needle unit to be inserted easily into the puncture device upon insertion of the puncture needle unit into the puncture device.

However, when the puncture needle unit is inserted into the puncture device, due to the clearance, the puncture needle unit may be inserted obliquely into the puncture device. In such a case, the puncture needle unit does not become properly mounted in the puncture device, i.e., the puncture needle of the puncture needle unit and the plunger of the puncture device do not become coupled to each other, thus making it difficult to puncture the fingertip with the puncture set.

Patent Document 1: International Publication No. 2006/028096

DISCLOSURE OF THE INVENTION

It is an object of the present invention to provide a puncture set, which allows the puncture needle of a puncture needle unit and the plunger of a puncture device to be reliably coupled to each other when the puncture needle unit is mounted in the puncture device.

To achieve the above object, there is provided in accordance with the present invention a puncture set comprising:

a puncture needle unit having a puncture needle including a needle body having a sharp needle point at a distal end thereof and a needle hub fixed to a proximal end of the needle body, and a tubular casing housing the puncture needle longitudinally movably therein and having an opening through which the needle point can project; and a puncture device having a housing, a ring-shaped mount disposed on a distal end portion of the housing for holding the casing removably mounted therein, and a plunger housed in the housing and having a coupling for being coupled to the needle hub in a mounted state in which the casing is mounted in the mount, wherein the casing has a plurality of casing protrusions that project on an outer circumferential surface thereof and which are disposed circumferentially along the outer circumferential surface, and the mount has a plurality of mount protrusions that project on an inner circumferential surface thereof and which are disposed circumferentially along the inner circumferential surface, at least one of the mount protrusions being positioned between an adjacent two of the casing protrusions in the mounted state.

With the above arrangement, when the puncture needle unit is mounted in the puncture device, the puncture needle of the puncture needle unit and the plunger of the puncture device are reliably coupled with each other.

In the puncture set according to the present invention, preferably, the needle hub includes a hollow cylindrical portion disposed on a proximal end portion thereof concentrically with the casing; and the coupling comprises a hollow cylindrical region disposed concentrically with the mount and fitted over the hollow cylindrical portion in the mounted state.

With this arrangement, when the puncture needle unit is pushed in toward the distal end with respect to the plunger, the puncture needle becomes coupled to the plunger without concern to the circumferential position thereof. Also, when the puncture needle unit is pulled toward the distal end, the puncture needle is released from the plunger.

In the puncture set according to the present invention, preferably, during a process of reaching the mounted state, the puncture needle unit is corrected to bring a central axis of the hollow cylindrical portion into alignment with a central axis of the coupling when at least one of the mount protrusions is positioned between an adjacent two of the casing protrusions.

With the above arrangement, when the puncture needle unit is mounted in the puncture device, the puncture needle of the puncture needle unit and the plunger of the puncture device are more reliably coupled with each other.

In the puncture set according to the present invention, preferably, during a process of reaching the mounted state, the mount protrusions have crests abutted against the outer circumferential surface of the casing, or the casing protrusions have crests abutted against the inner circumferential surface of the mount.

With the above arrangement, the puncture needle unit is reliably positioned radially with respect to the puncture device, and is reliably mounted in the puncture device.

In the puncture set according to the present invention, preferably, a number of the mount protrusions is equal to or greater than a number of the casing protrusions.

With the above arrangement, ease of operation when mounting the puncture needle unit in the puncture device is increased.

In the puncture set according to the present invention, preferably, the mount protrusions are disposed at equal angular intervals about a central axis of the mount.

With the above arrangement, immediately upon insertion of the puncture needle unit into the puncture device, at least one of the casing protrusions enters between the mount protrusions. The puncture needle unit is thereby prevented from rotating about its own axis, and is quickly corrected in attitude.

In the puncture set according to the present invention, preferably, each of the mount protrusions comprises a ridge that extends along a central axis of the mount.

With the above arrangement, when the puncture needle unit is mounted in the puncture device, a casing protrusion smoothly enters between two of the mount protrusions, thus allowing the puncture needle of the puncture needle unit to more reliably be coupled with the plunger of the puncture device.

In the puncture set according to the present invention, preferably, each of the mount protrusions extends from a distal end face of the mount, or from a position immediately close to the distal end face.

With the above arrangement, immediately upon insertion of the puncture needle unit into the puncture device, at least one of the casing protrusions enters between the mount protrusions. The puncture needle unit is thereby prevented from rotating about its own axis, and is quickly corrected in attitude.

In the puncture set according to the present invention, preferably, each of the mount protrusions has, on a distal end portion thereof, a height, a width, or a height and a width that are progressively reduced toward the distal end.

With the above arrangement, the puncture needle unit can easily be inserted into the puncture device.

In the puncture set according to the present invention, preferably, the casing protrusions are disposed at equal angular intervals about a central axis of the casing.

With the above arrangement, immediately upon insertion of the puncture needle unit into the puncture device, at least one of the casing protrusions enters between the mount protrusions. The puncture needle unit is thereby prevented from rotating about its own axis, and is quickly corrected in attitude.

In the puncture set according to the present invention, preferably, adjacent ones of the casing protrusions have different heights.

With the above arrangement, when the puncture needle unit is inserted (mounted) in the puncture device, crests of the higher casing protrusions are held in contact with the inner circumferential surface of the mount, while crests of the lower casing protrusions are held out of contact with the inner circumferential surface of the mount. As a result, the area of contact between the casing as a whole and the inner circumferential surface of the mount is reduced in order to allow the casing to be easily inserted into the mount.

In the puncture set according to the present invention, preferably, each of the casing protrusions comprises a ridge that extends along a central axis of the casing.

With the above arrangement, when the puncture needle unit is mounted in the puncture device, a casing protrusion smoothly enters between two mount protrusions, thus allowing the puncture needle of the puncture needle unit to be more reliably coupled with the plunger of the puncture device.

In the puncture set according to the present invention, preferably, each of the casing protrusions extends to a proximal end surface of the casing.

With the above arrangement, immediately upon insertion of the puncture needle unit into the puncture device, at least one of the casing protrusions enters between the mount protrusions. The puncture needle unit is thereby prevented from rotating about its own axis, and is quickly corrected in attitude.

In the puncture set according to the present invention, preferably, each of the casing protrusions has, on a proximal end portion thereof, a height, a width, or a height and a width that are progressively reduced toward the proximal end.

With the above arrangement, the puncture needle unit can easily be inserted into the puncture device.

In the puncture set according to the present invention, preferably, the puncture device has an ejection mechanism housed in the mount, and having an ejection member that covers the plunger.

With the above arrangement, the plunger is prevented from becoming displaced radially and is kept in a proper attitude. Therefore, when the puncture needle unit is mounted in the puncture device, the puncture needle is reliably coupled with the plunger of the puncture device.

In the puncture set according to the present invention, preferably, the ejection member has a plurality of ejection protrusions projecting on an outer circumferential surface thereof and disposed circumferentially along the outer circumferential surface, wherein, when at least one of the mount protrusions is positioned between an adjacent two of the ejection protrusions, the ejection member performs a guiding function to prevent the coupling from bending radially with respect to a central axis thereof and to fix the coupling and the plunger along the central axis.

With the above arrangement, for example, the ejection member can move stably within the housing and along the longitudinal direction of the housing.

In the puncture set according to the present invention, preferably, the needle hub comprises a hollow cylindrical portion having an outside diameter that progressively increases from a proximal end toward a distal end thereof.

With the above arrangement, when the puncture needle unit is mounted in the puncture device, the hollow cylindrical portion of the needle hub is easily inserted into the plunger, and hence the hollow cylindrical portion is reliably coupled with the plunger.

BEST MODE FOR CARRYING OUT THE INVENTION

A puncture set according to the present invention will be described in detail below based on a preferred embodiment thereof shown in the accompanying drawings.

Figure 1:
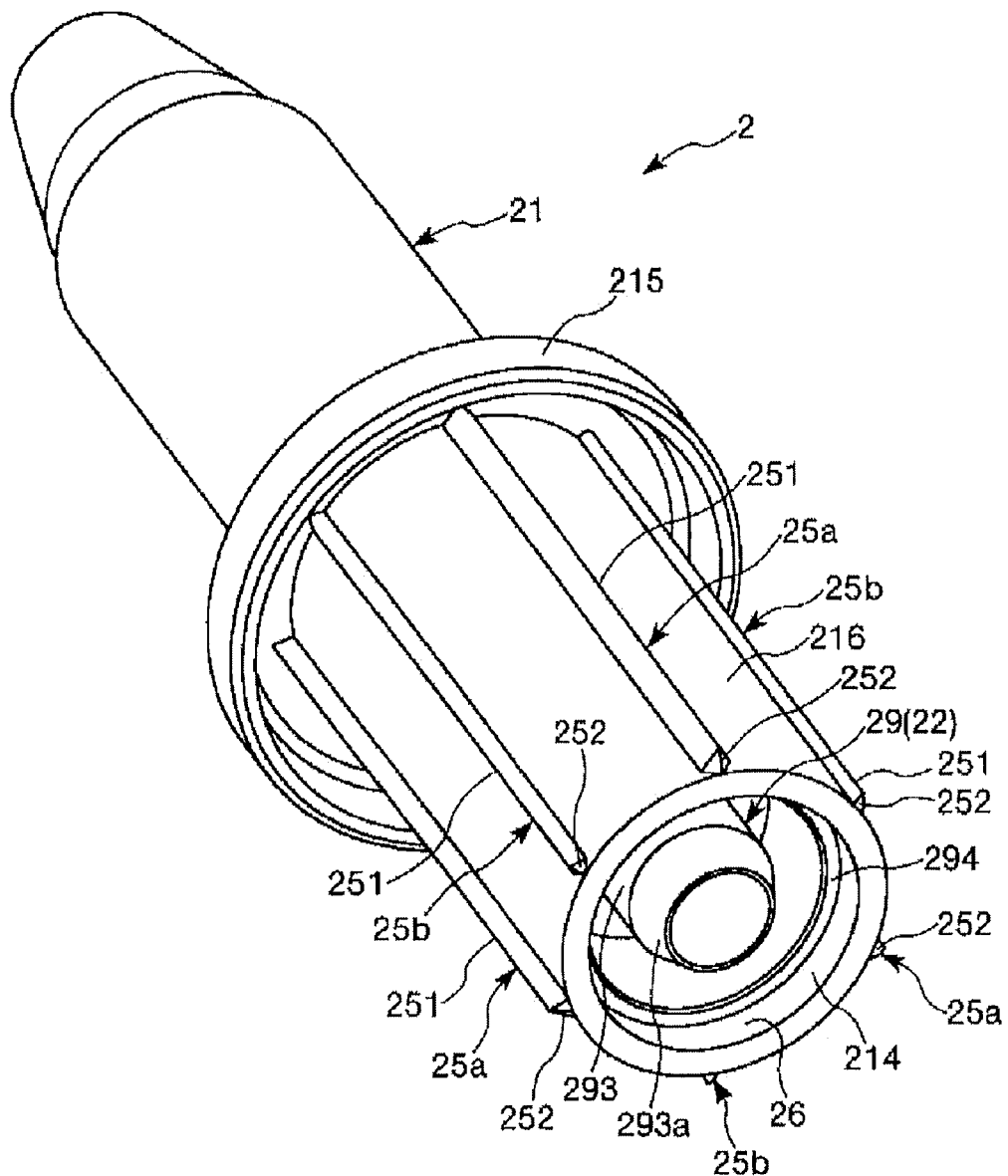
FIG. 1 is a perspective view of a puncture needle unit of a puncture set according to the present invention.
Figure 2:
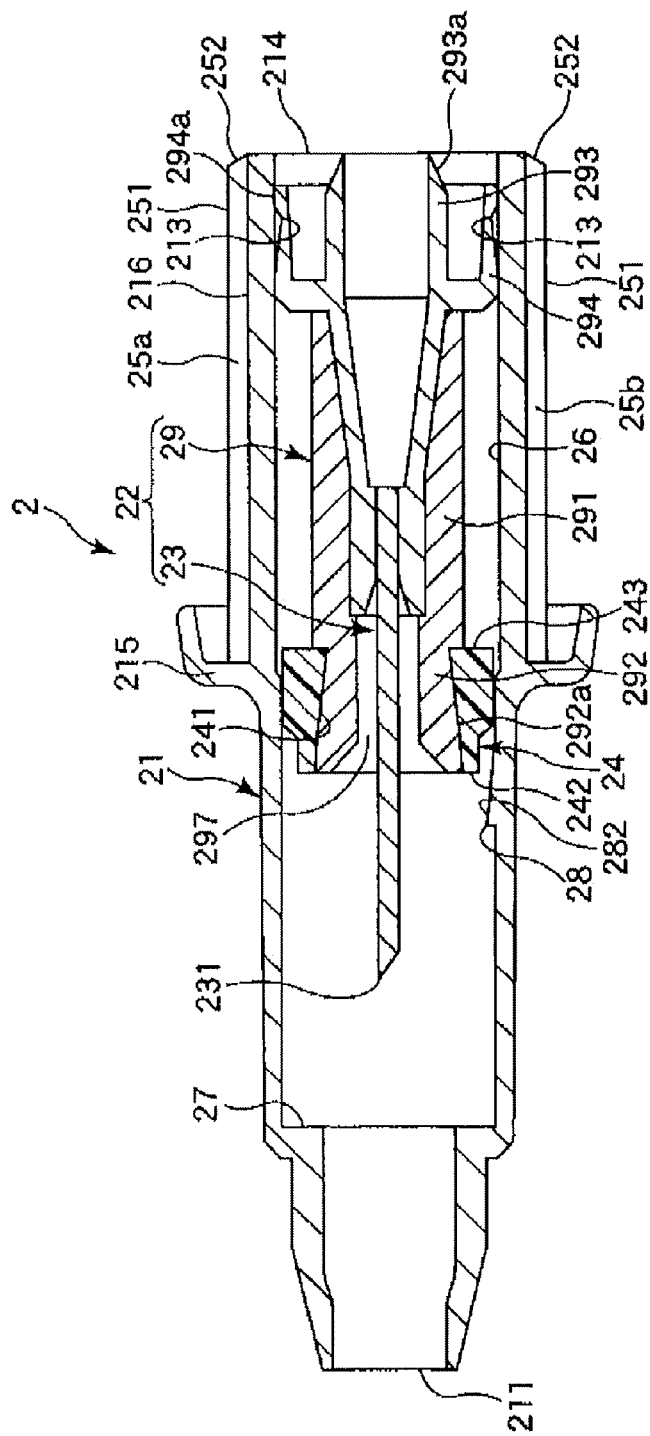
FIG. 2 is a longitudinal cross-sectional view of the puncture needle unit shown in FIG. 1.
Figure 3:
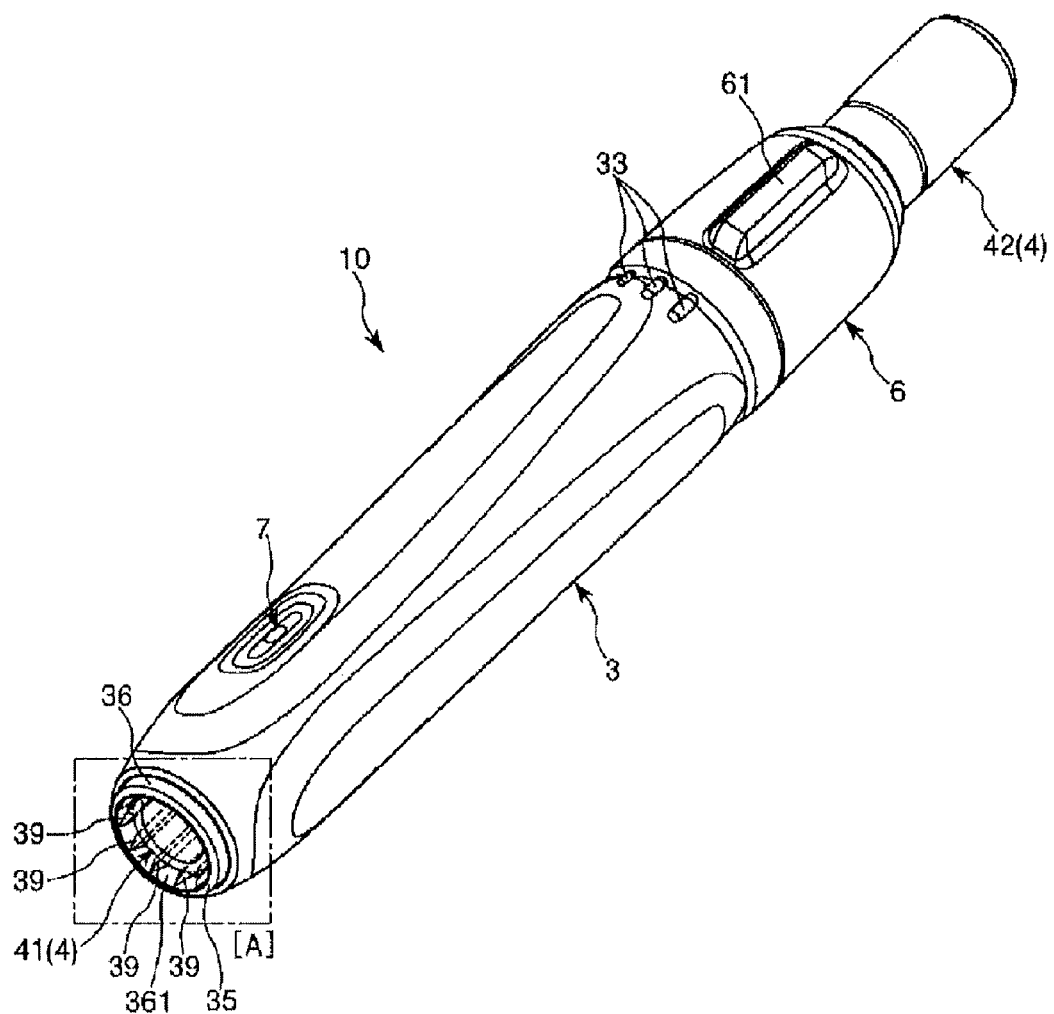
FIG. 3 is a perspective view of a puncture device of the puncture set according to the present invention.
Figure 4:
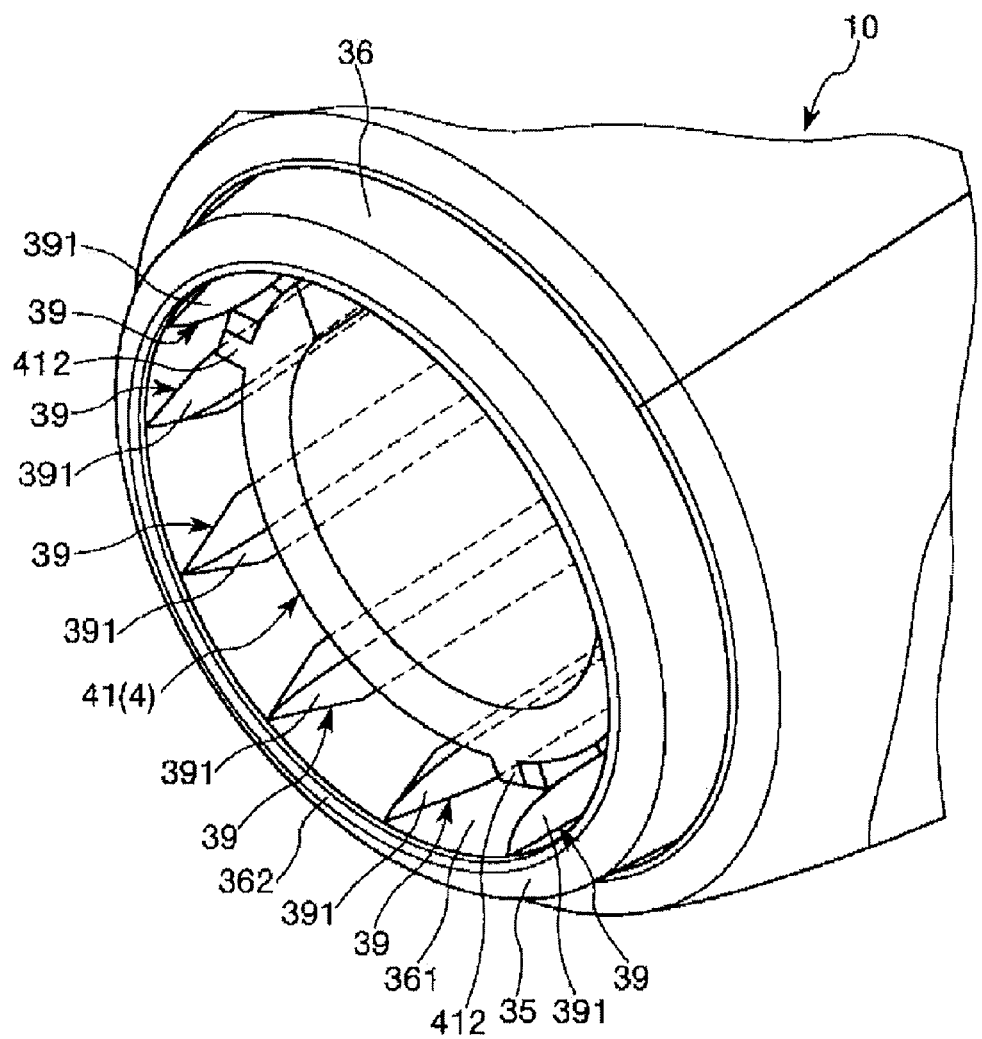
FIG. 4 is an enlarged detailed view of an area [A] enclosed by the dot-and-dash line shown in FIG. 3.
Figure 5:
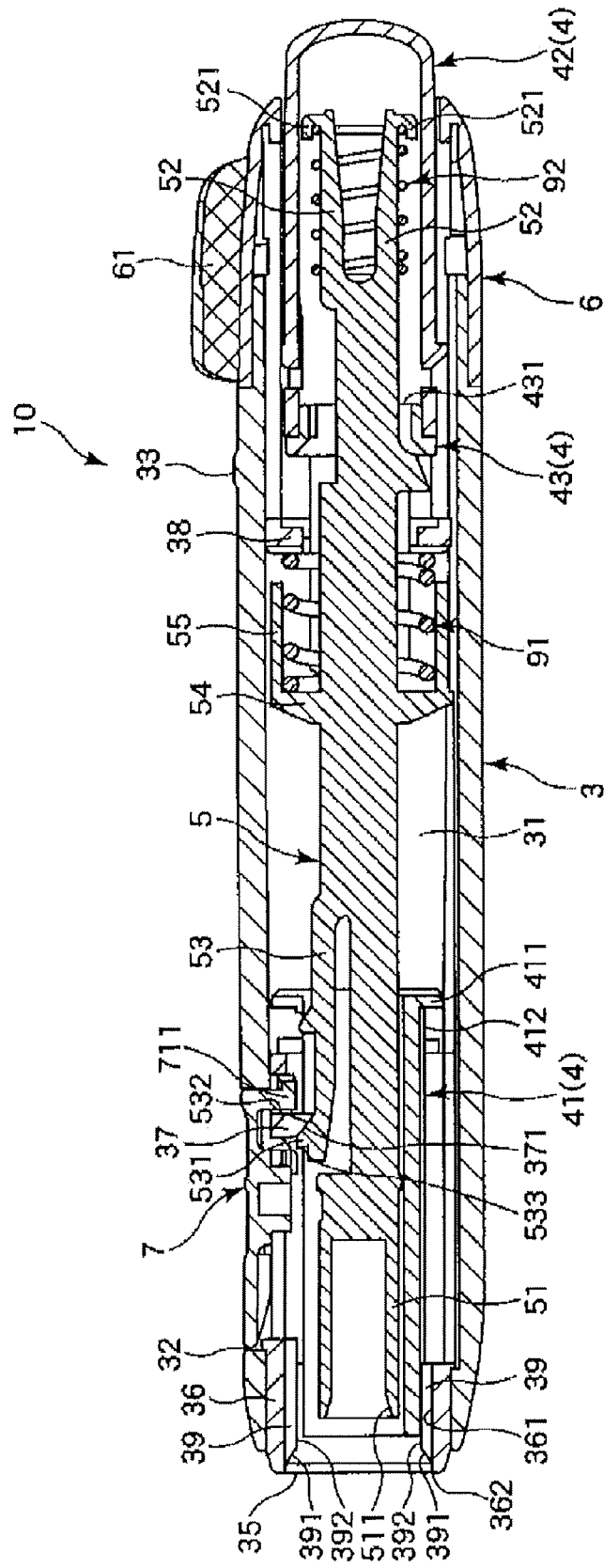
FIG. 5 is a longitudinal cross-sectional view of the puncture device shown in FIG. 3.
Figure 7:
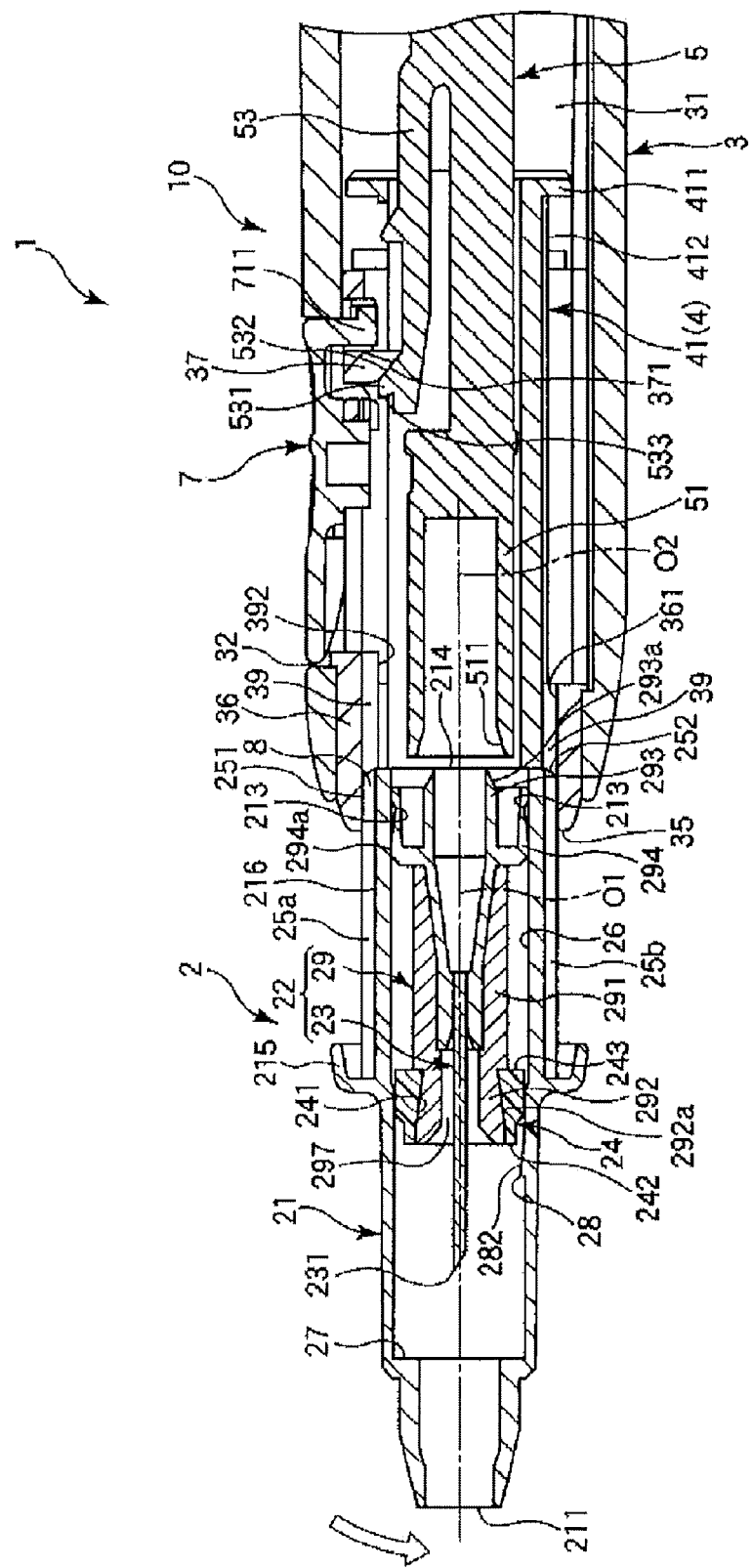
FIG. 7 is a longitudinal cross-sectional view showing the manner in which the puncture needle unit is mounted in the puncture device.
Figure 8:
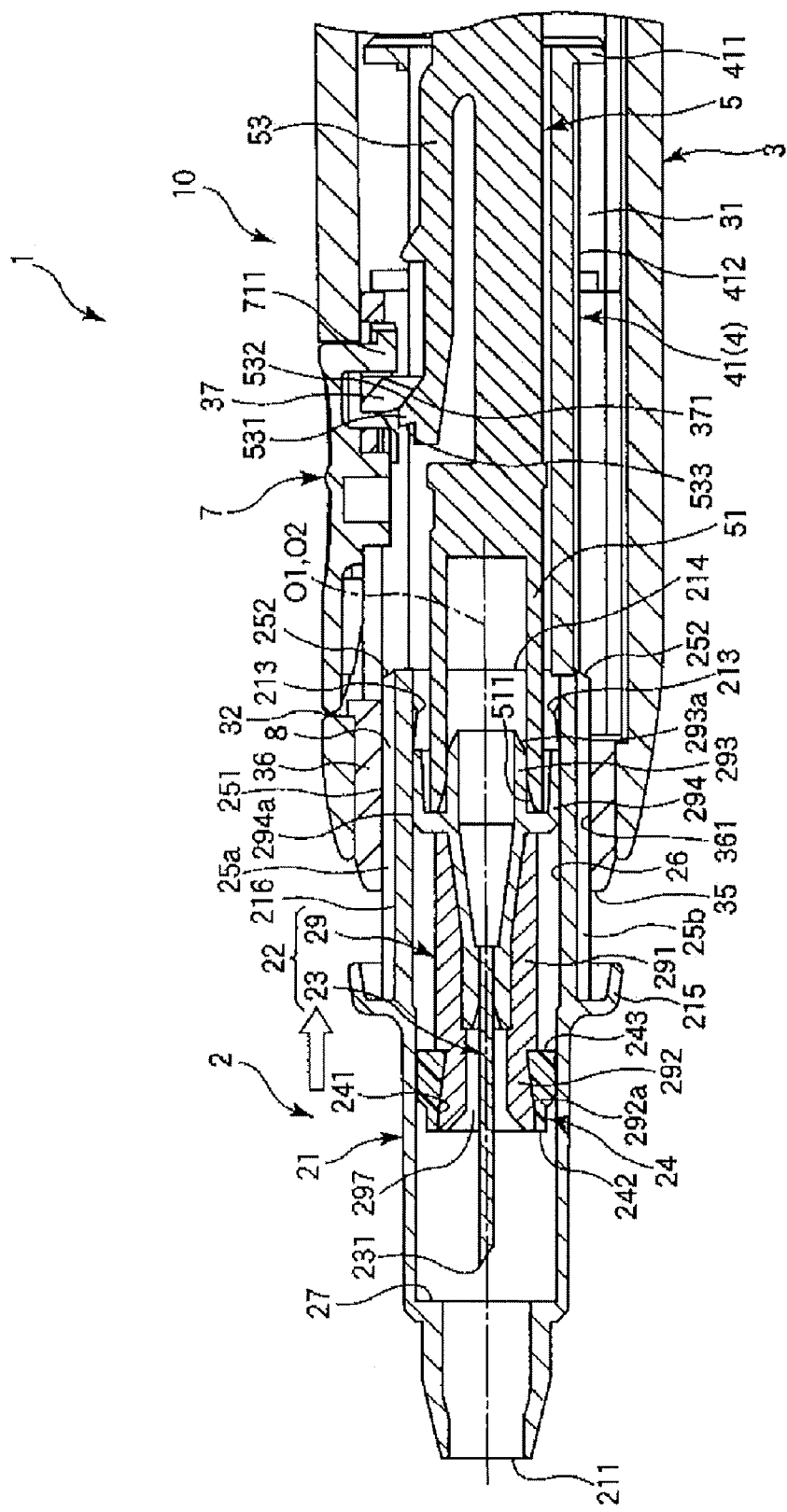
FIG. 8 is a longitudinal cross-sectional view showing the manner in which the puncture needle unit is mounted in the puncture device.
Figure 9:
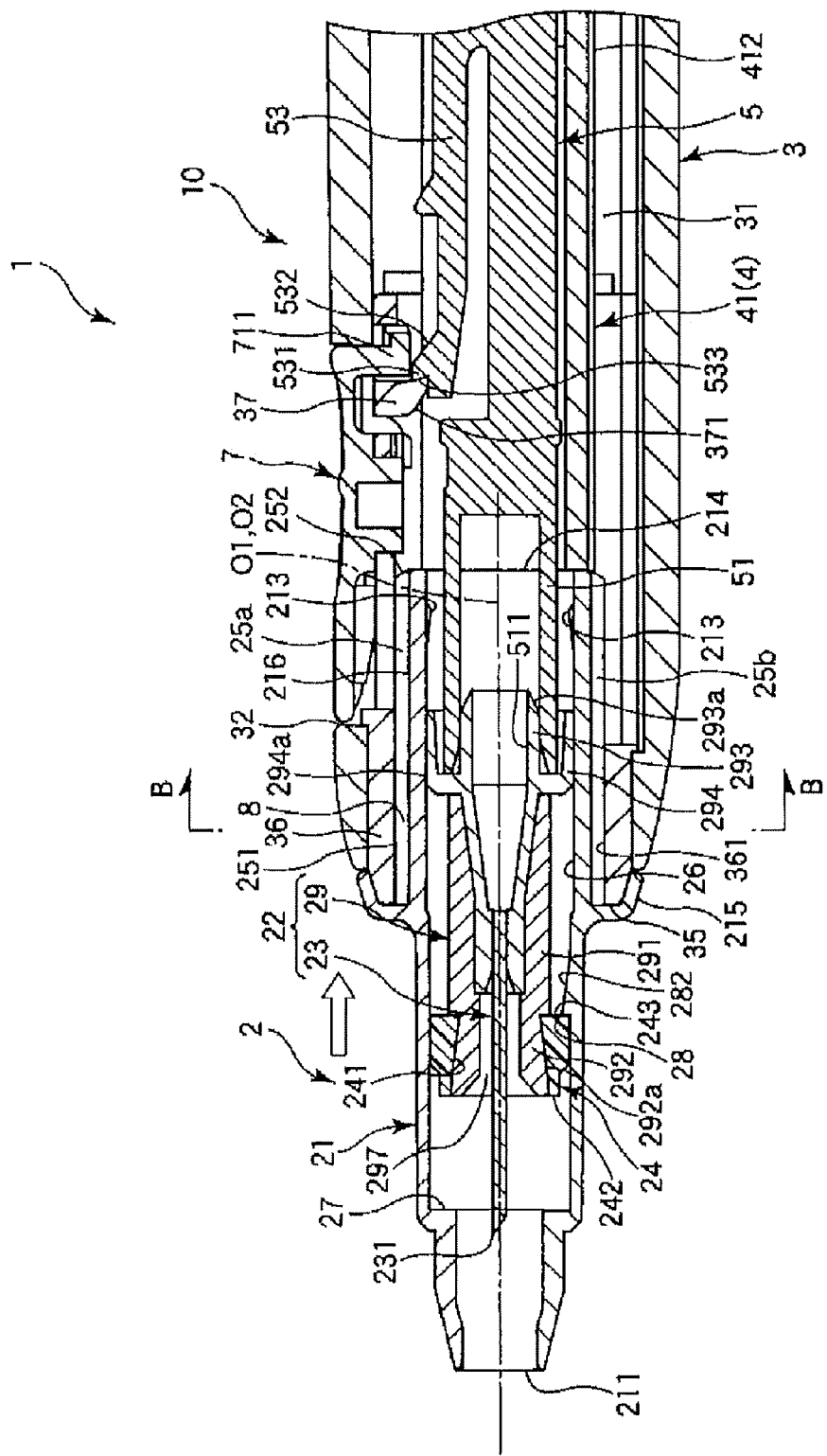
FIG. 9 is a longitudinal cross-sectional view showing the manner in which the puncture needle unit is mounted in the puncture device.
Figure 10:
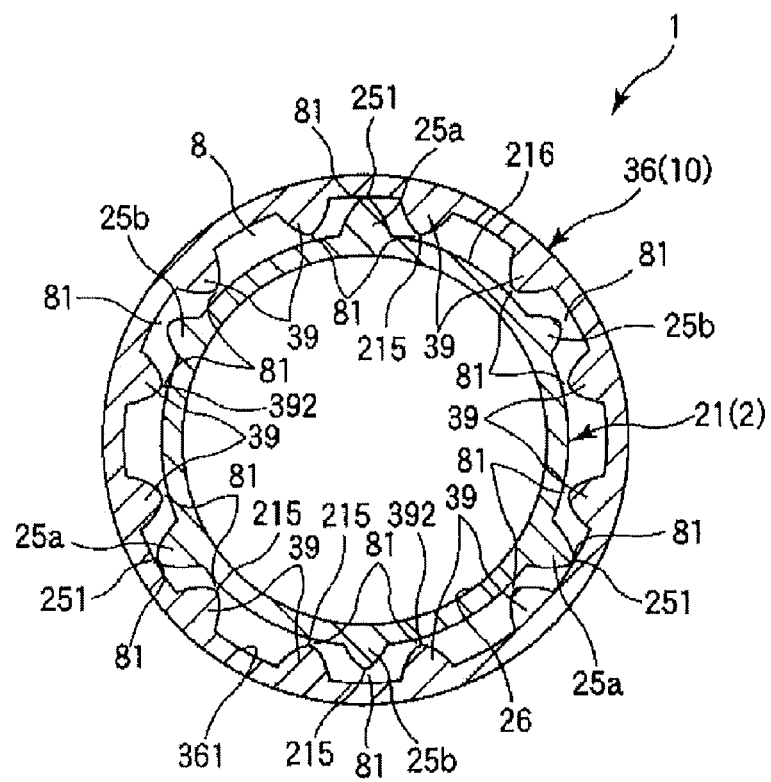
FIG. 10 is a cross-sectional view taken along line B-B of FIG. 9.

FIG. 1 is a perspective view of a puncture needle unit of a puncture set according to the present invention, FIG. 2 is a longitudinal cross-sectional view of the puncture needle unit shown in FIG. 1, FIG. 3 is a perspective view of a puncture device of the puncture set according to the present invention, FIG. 4 is an enlarged detailed view of an area [A] enclosed by the dot-and-dash line shown in FIG. 3, FIG. 5 is a longitudinal cross-sectional view of the puncture device shown in FIG. 3, FIGS. 6 to 9 are longitudinal cross-sectional views showing the manner in which the puncture needle unit is mounted in the puncture device, and FIG. 10 is a cross-sectional view taken along line B-B of FIG. 9. To facilitate the following descriptions, the right hand near side in FIG. 1 will be referred to as a "proximal end" and the left hand far side will be referred to as a "distal end". The right hand side in FIGS. 2 and 5 to 9 will be referred to as a "proximal end" and the left hand side will be referred to as a "distal end". The right hand far side in FIGS. 3 and 4 will be referred to as a "proximal end" and the left hand near side will be referred to as a "distal end". In FIG. 10, only the mount of a main body of the device and a casing of the puncture needle unit are illustrated, whereas other regions (members) have been omitted from illustration.

A puncture set 1 includes a puncture tool (puncture needle unit) 2 and a puncture device 10. The puncture set 1 is used to puncture the surface of a living body with the puncture tool 2 being mounted in the puncture device 10 (in the state shown in FIG. 9). After having punctured the surface of the living body, the puncture tool 2 can be removed from the puncture device 10. After use thereof, the puncture tool 2 is discarded, and an unused puncture tool 2 is newly mounted in the puncture device 10.

The puncture tool 2 will first be described below, and the puncture device 10 will be described thereafter.

The puncture tool 2, which is shown in FIGS. 1 and 2 (also FIGS. 6 to 9), has a hollow cylindrical (tubular) casing (puncture needle holder) 21, and a puncture needle 22 that is axially (longitudinally) movably housed within the casing 21. The puncture tool 2 also has a ring-shaped member 24 mounted on an outer circumferential surface (outer circumferential portion) 292a of an elastically deformable portion 292 of the puncture needle 22, to be described later.

As shown in FIG. 2, the puncture needle 22 has a needle body 23 and a needle hub (hereinafter referred to simply as a "hub") 29.

The needle body 23 has a sharp needle point 231 disposed (formed) on a distal end thereof. The needle point 231 is capable of puncturing the surface of a living body.

The needle body 23 may be made of materials that include, but are not limited to, various metal materials such as stainless steel, aluminum or aluminum alloys, titanium or titanium alloys, and superelastic alloys such as Ni—Ti alloy, as well as various hard resin materials such as polyphenylene sulfide, for example.

The hub 29 is fixed to a proximal end portion of the needle body 23. The hub 29 has a cylindrical hub body 291, an elastically deformable portion 292 that extends further toward the distal end from the distal end of the hub body 291, a mounted portion (hollow cylindrical portion) 293 disposed on the proximal end of the hub body 291, which is to be coupled with (mounted in) a plunger 5 of the puncture device 10, and a large-diameter portion 294 disposed around an outer circumferential surface of the mounted portion 293.

The mounted portion 293 comprises a hollow cylindrical member that projects integrally from the proximal end of the hub body 291. The mounted portion 293 (the hub 29) is disposed concentrically with the casing 21. The mounted portion 293 includes a tapered portion 293a on a distal end thereof whose outside diameter is progressively reduced toward the distal end. When the puncture tool 2 is mounted in the puncture device 10, the tapered portion 293a enables the mounted portion 293 to be inserted easily into the plunger 5 and hence to be reliably coupled to the plunger 5.

The large-diameter portion 294, which has a cup-like shape, is integrally formed with the hub body 291 around the outer circumferential surface of the mounted portion 293. The large-diameter portion 294 has an outside diameter, which is substantially the same as the inside diameter of an inner circumferential portion 26 of the casing 21. When the puncture needle 22 moves in and along the casing 21, an outer circumferential surface 294a of the large-diameter portion 294 slides along (i.e., is supported by) the inner circumferential surface 26 of the casing 21, thereby enabling the puncture needle 22 to move in a stable manner.

The elastically deformable portion 292 is of a hollow cylindrical shape in its entirety and has a pair of longitudinally defined cutouts (missing portions) 297, which enable the elastically deformable portion 292 to be easily deformed in a radial direction (i.e., vertically in FIG. 2). More specifically, the elastically deformable portion 292 can be elastically deformed between a radially contracted state, in which the elastically deformable portion 292 is closer to the needle body 23, and a radially expanded state, in which the elastically deformable portion 292 is positioned more remotely from the needle body 23. The ring-shaped member 24 is mounted in a free state on the elastically deformable portion 292. When the elastically deformable portion 292 is radially contracted, the ring-shaped member 24 can be released from the elastically deformable portion 292. A "free state" refers to a state in which no external force is applied to (imposed on) the elastically deformable portion 292.

The outer circumferential surface (outer circumferential portion) 292a of the elastically deformable portion 292 is of a tapered shape, having an outside diameter that is progressively reduced toward the proximal end, thereby preventing the ring-shaped member 24 from being unintentionally released from the elastically deformable portion 292.

As shown in FIG. 2, the ring-shaped member 24 forms a member that is released from the elastically deformable portion 292 after the puncture needle 22 has punctured the surface of the living body, and thus prevents the needle point 231 of the puncture needle 22 from projecting from an opening 211 of the casing 21.

The ring-shaped member 24 has an inner circumferential surface (inner circumferential portion) 241 having a tapered shape, the inside diameter of which is progressively reduced toward the proximal end. Since the inner circumferential surface 241 of the ring-shaped member 24 and the outer circumferential surface 292a of the elastically deformable portion 292 are both tapered in shape, when the ring-shaped member 24 is released from the elastically deformable portion 292 (in a released state), the elastically deformable portion 292 assumes a radially expanded state, wherein an outside diameter on the distal end thereof is greater than the inside diameter of the ring-shaped member 24 on the proximal end thereof. Therefore, the ring-shaped member 24 is prevented from being remounted again on the elastically deformable portion 292. In other words, the ring-shaped member 24 becomes irreversibly released from the elastically deformable portion 292.

The hub 29 and the ring-shaped member 24 are made of materials including, but not limited to, plastics and metal materials.

The puncture needle 22 is housed in the casing 21. The casing 21 comprises a hollow cylindrical member having an opening (distal end opening) 211 defined in the distal end thereof, which functions as a region that abuts against the surface of a living body, such as a fingertip, the palm of a hand, an upper arm, an abdominal region, a thigh, or an ear lobe. The casing 21 also has an opening (proximal end opening) 214 defined in the proximal end thereof.

The inner circumferential surface 26 of the casing 21 has a ring-shaped member abutment 27, an engaging portion 28, and a hub engaging portion 213.

The ring-shaped member abutment 27 comprises a step, which is formed by reducing the inside diameter of a distal end portion of the inner circumferential surface 26. The ring-shaped member abutment 27 is brought into abutment against a distal end face 242 of the ring-shaped member 24, which is released from the hub 29 (the elastically deformable portion 292) of the puncture needle 22 (in a released state), thereby preventing the ring-shaped member 24 from moving beyond the ring-shaped member abutment 27 toward the distal end.

The engaging portion 28 comprises a protrusion that projects from the inner circumferential surface 26, at a middle position along the longitudinal direction of the casing 21. The engaging portion 28 has a slanted surface 282 on a proximal end portion thereof. When the puncture needle 22 moves toward the distal end, the ring-shaped member 24 can move over and past the slanted surface 282 (see FIG. 9).

When the casing 21 of the puncture tool 2 is gripped, and the puncture tool 2 is pulled toward the distal end and is removed from the puncture device 10 in the state shown in FIG. 9, i.e., after having punctured the surface of a living body, since the casing 21 first moves toward the distal end, the puncture needle 22, which is coupled to the plunger 5, is moved (pulled) relatively toward the proximal end until a proximal end surface 243 of the ring-shaped member 24, which is mounted on the elastically deformable portion 292 (in a mounted state), abuts against (engages with) the engaging portion 28. The ring-shaped member 24 is thus prevented (limited) from moving away from the engaging portion 28 toward the distal end. From this state, as the casing 21 moves further toward the distal end, the elastically deformable portion 292 is moved relatively toward the proximal end while becoming deformed (so as to assume the radially contracted state), with the outer circumferential surface 292a being pressed by the inner circumferential surface 241 of the ring-shaped member 24, until finally the ring-shaped member 24 becomes released from the elastically deformable portion 292. The puncture needle 22 is limited against further movement due to the fact that the large-diameter portion 294 is locked (engaged) again by the hub engaging portion 213 of the casing 21. In other words, the puncture needle 22 is prevented from becoming released from the proximal end of the casing 21. The force applied to release the hub 29 from the plunger 5 is set to a level greater than the force applied to release the ring-shaped member 24 from the elastically deformable portion 292. Consequently, the ring-shaped member 24 is reliably released from the elastically deformable portion 292 before the puncture needle 22 is released from the plunger 5. The puncture tool 2 is removed from the puncture device 10 when the puncture tool 2 is pulled further toward the distal end.

The ring-shaped member 24, which is released from the elastically deformable portion 292, is positioned between the ring-shaped member abutment 27 of the casing 21 and the elastically deformable portion 292 of the puncture needle 22. Therefore, even if the puncture needle 22 moves toward the distal end, the ring-shaped member 24 limits the range of movement of the puncture needle 22 toward the distal end within a range that prevents the needle point 231 from projecting from the opening 211. Therefore, when the puncture tool 2 is discarded, the needle point 231 is prevented from injuring the skin or causing infections.

When the puncture tool 2 is before use, the hub engaging portion 213 on the inner circumferential surface 26 of the casing 21 engages with the outer circumferential surface 294a of the large-diameter portion 294 of the hub 29. As shown in FIG. 2, since the large-diameter portion 294 is engaged (locked) by the hub engaging portion 213, the puncture needle 22 is prevented from being released from the proximal end of the casing 21.

A ring-shaped flange 215 is disposed on an outer circumferential surface 216 of the casing 21, so as to cover a distal end 35 of a mount 36 of the puncture device 10 when the puncture tool 2 is mounted on the puncture device 10. When the flange 215 covers the distal end 35 of the mount 36 in the mounted state, the puncture tool 2 becomes positioned with respect to the puncture device 10 (see FIG. 9).

The outside diameter of a portion of the outer circumferential surface 216 of the casing 21, which extends from the flange 215 toward the proximal end, may be constant along the longitudinal direction of the casing 21. Preferably, however, the outside diameter should be progressively reduced toward the proximal end.

The casing 21 is made of materials that may be, but are not limited to, the same materials used for the hub 29 as described above, for example.

Next, the puncture device 10 will be described below.

The puncture device 10 comprises an elongate housing 3, a plunger 5, an ejection mechanism 4, an adjuster (adjusting dial) 6, a puncture activator (activating means) 7, a coil spring 91 that biases the plunger 5 toward the distal end, and a coil spring 92 that biases the plunger 5 toward the proximal end.

As shown in FIGS. 3 and 5, the housing 3 comprises a tubular member, i.e., a hollow region 31 which opens in the distal end and in the proximal end, and also functions as a grip when the puncture device 10 is used. A puncture mechanism, including the coil spring 91 that biases the plunger 5 toward the distal end and the coil spring 92 that biases the plunger 5 toward the proximal end, are disposed (housed) in the hollow region 31 together with a portion of the ejection mechanism 4.

The mount 36, in which the casing 21 of the puncture tool 2 is removably mounted, is disposed on the distal end portion of the housing 3. The mount 36 comprises a ring-shaped member, which is fixed to the distal end portion of the housing 3 by fitting engagement, bonding (adhesive or solvent bonding), fusion (thermal fusion, high-frequency fusion, ultrasonic fusion, etc.), or the like. As shown in FIG. 4, the mount 36 has an inner circumferential surface 361 having a rounded distal end portion (distal end inner circumferential surface 362). When the puncture tool 2 is mounted in the puncture device 10, the casing 21 of the puncture tool 2 is guided into the mount 36 by the distal end inner circumferential surface 362 of the mount 36. Accordingly, the puncture tool 2 is easily mounted in the puncture device 10.

The inside diameter of the inner circumferential surface 361 of the mount 36 may be constant along the axis of the mount 36, but preferably, should be progressively reduced toward the proximal end. More preferably, the inside diameter of the inner circumferential surface 361 should be constant over a certain distance thereof from the distal end, and then decrease progressively toward the proximal end.

The puncture activator 7 in the form of a plate, and a plurality of (three in the structure shown in FIG. 3) indicia 33 are disposed on an upper side of the housing 3, as shown in FIG. 5. The puncture activator 7 is disposed near the distal end of the housing 3, while the indicia 33 are disposed near the proximal end of the housing 3.

The puncture activator 7 defines a region (member) to be pressed when the puncture device 10 is activated. The puncture activator 7 is disposed in an opening 32 opened in the wall of the housing 3, and can be pressed toward the hollow region 31 (plunger 5) of the housing 3. A projection 711 projects downwardly as shown in FIG. 5, from a reverse side (lower side in FIG. 5) of the puncture activator 7. When the puncture activator 7 is pressed, while the puncture set 1 is in a puncture-enabled state (i.e., the state shown in FIG. 9), the projection 711 releases an engaging portion 531 of the plunger 5 as described later and a stopper 37 of the housing 3 out of engagement with each other.

The adjuster 6, which is tubular in shape, is disposed (supported) on a proximal end portion of the housing 3 while being rotatable about the axis of the housing 3. The adjuster 6 has a lever 61, which is engaged by a finger in order to rotate the adjuster 6, so as to align the lever 61 with (cause the lever 61 to correspond to) a desired one of the indicia 33. By thus rotating the adjuster 6, the distance that the plunger 5 moves in the longitudinal direction of the housing 3 can be adjusted. In the puncture device 10, the distance that the plunger 5 moves toward the distal end, i.e., the distance that the puncture needle 22 (the needle point 231) projects, can be changed depending on the position of the adjuster 6. Therefore, the depth at which the puncture needle 22 punctures the surface of the living body can be adjusted depending on individual differences of persons (examinees) from whom blood is sampled, or depending on the body region to be punctured.

As shown in FIG. 5, the plunger 5, which is movable along its own axis, is disposed (housed) in the housing 3.

The plunger 5 is of an elongate shape and has a coupling 51 on a distal end portion thereof, on which the puncture needle 22 of the puncture tool 2 is removably mounted (coupled). The coupling 51 has a hollow cylindrical shape concentric with the mount 36 of the housing 3. When the puncture needle 22 is mounted, the mounted portion 293 of the puncture needle 22 is inserted into the coupling 51, which is fitted over the mounted portion 293. When the puncture tool 2 is pushed into the plunger 5 (the coupling 51) toward the proximal end, the puncture needle 22 is coupled to the plunger 5 through the coupling 51. When the puncture tool 2 is pulled toward the distal end, the puncture needle 22 becomes released from the plunger 5. The coupling 51 has on its distal end portion a tapered portion 511, the inside diameter of which decreases progressively toward the proximal end. When the puncture tool 2 is mounted in the puncture device 10, the tapered portion 511 allows the mounted portion 293 of the puncture needle 22 to be easily inserted into the coupling 51.

The plunger 5 has a ring-shaped flange 54 on a middle portion thereof, which has a wall 55 erected from the edge thereof toward the proximal end. The flange 54 functions as a spring seat against which a distal end of the coil spring 91 is abutted. The wall 55 is abutted against an outer circumferential surface of the coil spring 91 in order to prevent the coil spring 91 from buckling, i.e., so as to allow the coil spring 91 to be deformed (expanded and compressed) in a stable manner.

The proximal end of the coil spring 91 is abutted against a ring-shaped spring seat 38, which is disposed in the housing 3 in concentric relation thereto. When the plunger 5 moves toward the proximal end, the coil spring 91 is compressed between the flange 54 and the spring seat 38, thereby accumulating energy for moving the plunger 5 toward the distal end. The coil spring 91 thus functions as a puncture spring, which is used to puncture the surface of a living body.

The plunger 5 has a pair of fingers 52, 52 disposed on the proximal end thereof, which project in the direction toward the proximal end. Each of the fingers 52 has a barb 521 on the proximal end thereof, which is folded back toward the distal end. Each of the barbs 521 serves as a spring seat, which grips and secures the proximal end of the coil spring 92. When the puncture tool 2 is not mounted in the puncture device 10, the coil spring 92 essentially is placed in an unloaded state (at its natural length) (see FIG. 5). When the puncture tool 2 is mounted in the puncture device 10, the coil spring 92 is abutted against a proximal end surface 431 of a coupling 43 of the ejection mechanism 4, as will be described later. When the puncture tool 2 is mounted in the puncture device 10 and is activated to puncture the surface of the living body, i.e., when the plunger 5 moves toward the distal end, the coil spring 92 becomes compressed between the barbs 521 and the coupling 43, thereby accumulating energy which is used to return the plunger 5 toward the proximal end. The coil spring 92 thus functions as a return spring, which is used to return the plunger 5 to its original position (the position prior to puncturing).

The coil springs 91, 92 have various parameters such as spring constants, axial lengths, etc., which are set to appropriate values.

The plunger 5 also has a lock member 53 in the form of an elastically deformable plate (comprising a plate), which is disposed between the coupling 51 and the flange 54. The lock member 53 has the proximal end thereof supported in a cantilevered fashion.

The lock member 53 has an engaging portion 531 disposed near the free end (distal end) thereof, which projects upwardly as shown in FIG. 5. The engaging portion 531 has a slanted surface 532 on the proximal end thereof. In the state shown in FIG. 5 (in which the puncture tool 2 is not mounted in the puncture device 10), the slanted surface 532 is abutted against a slanted surface 371 of the stopper 37, which is in the form of a block, in the housing 3. When the puncture device 10 is completely prepared (set) for performing a puncture, i.e., when the puncture tool 2 is mounted in the puncture device 10, the engaging portion 531 moves over and past the stopper 37 as the plunger 5 is pressed toward the proximal end by the puncture needle 22. At this time, the plunger 5 is biased toward the distal end by the coil spring 91, and the engaging portion 531 has a distal end face 533 that is abutted against the stopper 37 and locked with respect to the housing 3 (see FIG. 9). The engaging portion 531 can be unlocked when the puncture activator 7 is pressed, as described above. When the engaging portion 531 becomes unlocked, the plunger 5 moves toward the distal end under the biasing force of the coil spring 91 and punctures the surface of the living body.

The ejection mechanism 4 is disposed in the housing 3. The ejection mechanism 4 is a mechanism for releasing (removing) the puncture tool 2 mounted in the puncture device 10 from the puncture device 10. The ejection mechanism 4 comprises an ejection member (ejector) 41, a coupling 43, and an ejection button 42, which are successively arranged in this order from the distal end.

The ejection member 41 is a member for pushing (pressing) the puncture tool 2 mounted in the puncture device 10 toward the distal end. The ejection member 41 comprises a tubular member having a C-shaped transverse cross section (see FIG. 4). The ejection member 41 is housed in the mount 36 and is disposed around the outer circumferential surface of the coupling 51 of the plunger 5 in concentric relation to the coupling 51 (see FIG. 5).

As shown in FIG. 4, the ejection member 41 has a plurality of ribs (ridges, ejection protrusions) 412 disposed on an outer circumferential surface along the longitudinal direction thereof. The ribs 412 are disposed at equal angular intervals about the central axis of the ejection member 41. The ribs 412 are positioned between a plurality of mount ribs 39, to be described later, on the inner surface of the mount 36, thereby allowing the ejection member 41 to move stably within the housing 3 (the mount 36) along the longitudinal direction of the housing 3. The ejection member 41 also has a flange 411 on the proximal end thereof, which has an increased outside diameter.

Since the coupling 51 of the plunger 5, which is disposed in the ejection member 41, is supported by the ejection member 41, the coupling 51 is prevented from becoming radially displaced (from being unintentionally displaced positionally). Therefore, when the puncture tool 2 is mounted in the puncture device 10, the mounted portion 293 of the puncture needle 22 is reliably coupled to the coupling 51 of the plunger 5 of the puncture device 10.

The ejection button 42 is a member used to actuate the ejection member 41. As shown in FIG. 5, the ejection button 42 comprises a bottomed tubular (cap-shaped) member, which is inserted in the proximal end portion of the housing 3.

The coupling 43, which is elongate in shape, is disposed between the ejection member 41 and the ejection button 42, and interconnects the ejection member 41 and the ejection button 42 with each other. When the ejection button 42 is pressed, the pressing force is transmitted through the coupling 43 to the ejection member 41.

The housing 3 (the mount 36), the ejection member 41, the ejection button 42, the coupling 43, the plunger 5, the adjuster 6, the puncture activator 7, and the coil springs 91, 92, which make up the puncture device 10, are made of materials which may be, but are not limited to, the same materials used for the hub 29, as described above, for example.

As shown in FIG. 1 (also in FIGS. 2 and 6 to 10), the outer circumferential surface 216 of the casing 21 has a plurality of (three in the present embodiment) first casing ribs (first casing protrusions) 25a, together with a plurality of (three in the present embodiment) second casing ribs (second casing protrusions) 25b that project therefrom. As shown in FIG. 4 (also in FIGS. 3 and 5 to 10), the inner circumferential surface 361 of the mount 36 of the puncture device 10 includes a plurality of (twelve in the present embodiment) mount ribs (mount protrusions) 39 that project therefrom.

Each of the first casing ribs 25a comprises a ridge that extends along the central axis of the casing 21. The three first casing ribs 25a, each comprising such a ridge, are disposed at equal angular intervals about the central axis of the casing 21 circumferentially along the outer circumferential surface 216 of the casing 21. As with the first casing ribs 25a, each of the second casing ribs 25b comprises a ridge that extends along the central axis of the casing 21. Each of the second casing ribs 25b is disposed between an adjacent two of the first casing ribs 25a. With the puncture tool 2, therefore, the three first casing ribs 25a and the three second casing ribs 25b are alternately disposed at equal angular intervals about the central axis of the casing 21, and circumferentially along the outer circumferential surface 216 of the casing 21 (see FIG. 10). Each of the second casing ribs 25b is smaller in height than each of the first casing ribs 25a. Each of the first casing ribs 25a and each of the second casing ribs 25b have widths, which are progressively smaller toward a crest 251 thereof.

Each of the mount ribs 39 comprises a ridge that extends along the central axis of the mount 36. Twelve mount ribs 39, each comprising such a ridge, are disposed at equal angular intervals about the central axis of the mount 36 and circumferentially along the inner circumferential surface 361 of the mount 36 (see FIG. 10). As with each of the first casing ribs 25a and each of the second casing ribs 25b, each of the mount ribs 39 has a width that becomes progressively smaller toward a crest 392 thereof.

Figure 6:
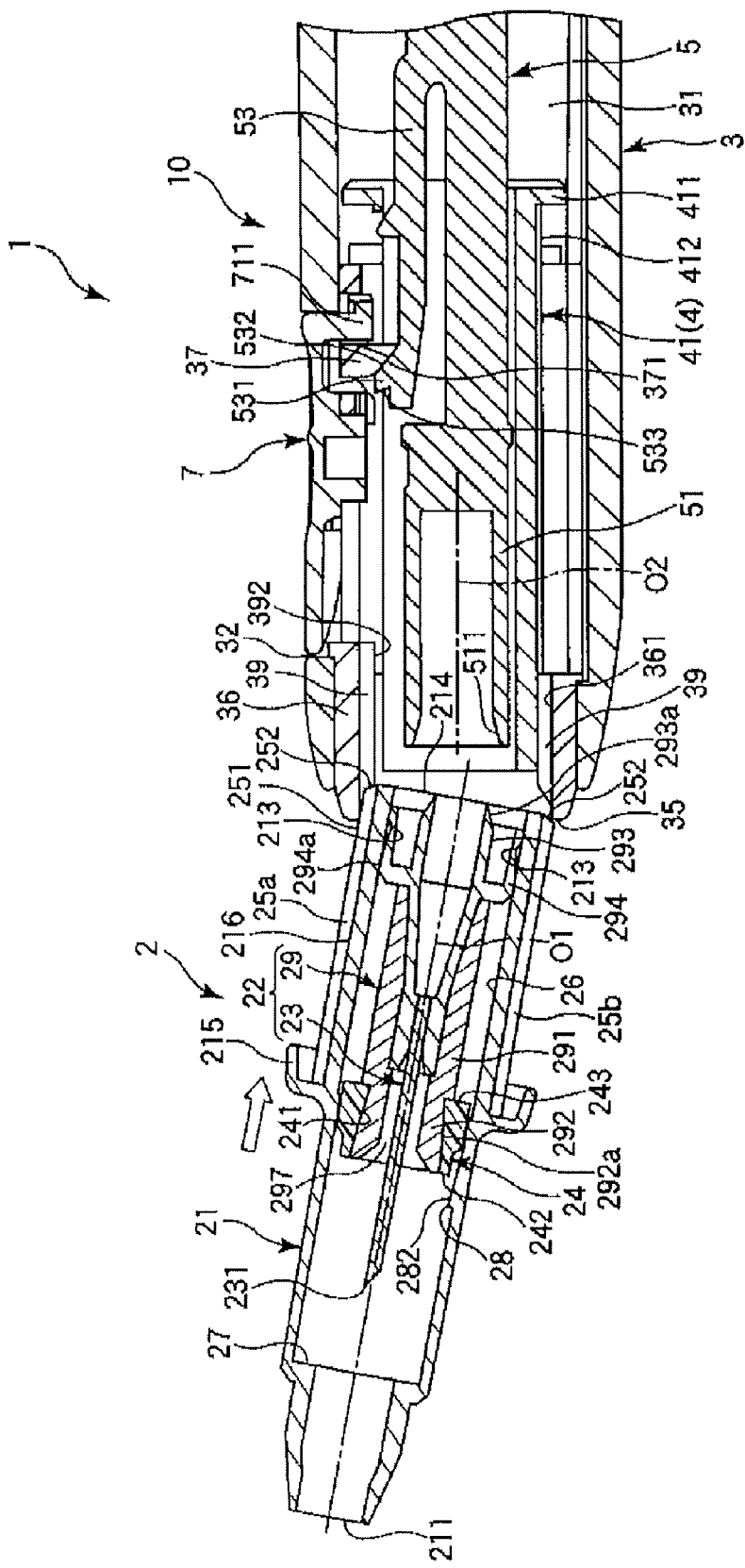
FIG. 6 is a longitudinal cross-sectional view showing the manner in which the puncture needle unit is mounted in the puncture device.

In order to mount the puncture tool 2 in the puncture device 10, the puncture tool 2 (mounted portion 293 of the puncture needle 22) should preferably be inserted at an attitude such that a central axis O1 of the puncture tool 2 and a central axis O2 of the puncture device 10 (coupling 51 of the plunger 5) are in coaxial alignment with each other. However, it is difficult to insert the puncture tool 2 with such accuracy. Actually, as shown in FIG. 6, for example, the puncture tool 2 may often be inserted at an improper attitude, which is oblique to the puncture device 10. If the puncture tool 2 is inserted as shown in FIG. 6, then since the central axis O1 of the puncture tool 2 and the central axis O2 of the puncture device 10 are not in coaxial alignment with each other, a difficulty may be encountered when the mounted portion 293 of the puncture needle 22 of the puncture tool 2 and the coupling 51 of the plunger 5 of the puncture device 10 are coupled to each other.

However, the puncture set 1 is effective to prevent such a difficulty from occurring. This preventive process will be described below with reference to FIGS. 6 to 10.

As shown in FIG. 6, the puncture tool 2 initially is inserted into the puncture device 10 while the central axis O1 of the puncture tool 2 is oblique to the central axis O2 of the puncture device 10.

When the puncture tool 2 is further inserted into the puncture device 10 from the state shown in FIG. 6, each casing rib 25a or 25b enters (is positioned) between adjacent ones of the mount ribs 39, which are arranged circumferentially along the inner circumferential surface 361 of the mount 36, in a space (gap) 8 between the outer circumferential surface 216 of the casing 21 and the inner circumferential surface 361 of the mount 36, thereby creating a plurality of (six in the structure shown in FIG. 10) areas of reduced gap length (small spaces 81). Since the gap is reduced, the puncture tool 2 is corrected in order to bring the central axis O1 thereof into alignment with the central axis O2 of the puncture device 10, before the puncture needle 22 (mounted portion 293) becomes coupled to the plunger 5 (coupling 51), as shown in FIG. 7.

During the process of inserting the puncture tool 2 into the puncture device 10, the crests 251 of the first casing ribs 25a abut against the inner circumferential surface 361 of the mount 36. Therefore, the puncture tool 2 is completely positioned radially (vertically in FIG. 7) with respect to the puncture device 10, and becomes reliably mounted in the puncture device 10.

When the puncture tool 2 is pushed in toward the proximal end from the state shown in FIG. 7, the mounted portion 293 of the puncture needle 22 becomes reliably coupled to the coupling 51 of the plunger 5 (see FIG. 8). At the same time, the hub engaging portion 213 of the casing 21 is released from engagement with the puncture needle 22 (see FIG. 8).

When the puncture tool 2 is pushed in from the state shown in FIG. 8 until the flange 215 of the casing 21 covers the distal end 35 of the mount 36, the puncture tool 2 becomes reliably mounted in the puncture device 10, thus bringing the puncture tool 2 into a state capable of puncturing the surface of the living body (see FIG. 9). In such a mounted state, since the crests 251 of the first casing ribs 25a are held in abutment against the inner circumferential surface 361 of the mount 36, the casing 21 of the puncture tool 2 is fitted into the mount 36 of the puncture device 10 (see FIG. 10). Thereby, the puncture tool 2 is prevented from being released from the puncture device 10.

Therefore, the puncture set 1 maintains the gap 8, which is required for insertion of the puncture tool 2 into the puncture device 10, while at the same time the gap length thereof is minimized, thereby reliably preventing the aforementioned difficulty from occurring.

The gap length of the small spaces 81 should preferably be, but is not limited to, 0 to 0.2 mm, and more preferably, 0 to 0.05 mm, for example.

As described above, each of the second casing ribs 25b is smaller in height than each of the first casing ribs 25a. In other words, in the puncture tool 2, the first casing ribs 25a and the second casing ribs 25b, which are adjacent to each other, are of different heights. Consequently, when the puncture tool 2 is inserted (mounted) in the puncture device 10, the crests 251 of the first casing ribs 25a are held in contact with the inner circumferential surface 361 of the mount 36, whereas the crests 251 of the second casing ribs 25b are held out of contact with the inner circumferential surface 361 of the mount 36. As a result, the area of contact between the casing 21 as a whole and the inner circumferential surface 361 of the mount 36 is reduced in order to allow the casing 21 to be easily inserted into the mount 36.

The height of the mount ribs 39 is substantially the same as the height of the second casing ribs 25b.

The height of the first casing ribs 25a should preferably be, but is not limited to, 0.3 to 1.1 mm, and more preferably, 0.4 to 0.8 mm, for example.

The height of the second casing ribs 25b should preferably be, but is not limited to, 0.2 to 1.0 mm, and more preferably, 0.3 to 0.7 mm, for example.

The mount ribs 39 are not limited to any particular height, length, width or shape. However, preferably, the height of the mount ribs 39 should be 0.2 to 1.0 mm, and more preferably, 0.3 to 0.7 mm. The length of the mount ribs 39 should preferably be 5 to 20 mm, and more preferably, 13 to 17 mm. The width of the mount ribs 39 should preferably be 0.5 to 2 mm, and more preferably, 0.8 to 1.2 mm. Each of the mount ribs 39 may be in the shape of a quadrangular prism, a triangular prism, a semicylinder, or the like. In the case of a quadrangular prism, the quadrangular prism should preferably have a trapezoidal cross section, the width of which becomes progressively smaller toward the crest.

As described above, the total number of ribs of the mount 36 (the mount ribs 39) is twelve, whereas the total number of ribs of the casing 21 (the first casing ribs 25a and the second casing ribs 25b) is six. In other words, in the puncture set 1 (puncture tool 2), the total number of ribs of the mount 36 is greater than the total number of ribs of the casing 21, so as not to lower the ease of operability with which the puncture tool 2 can be mounted in the puncture device 10.

According to the present embodiment, the number of ribs of the mount 36 is twelve and the number of ribs of the casing 21 is six. However, the ribs are not limited to such quantities, but may consist of any combination of numbers, each in the range of from 3 to 50.

As shown in FIG. 1 (and also in FIG. 2), each of the first casing ribs 25a and the second casing ribs 25b extends from a position near the flange 215 of the casing 21 toward the proximal end (the opening 214) of the casing 21. As shown in FIG. 4 (and also in FIG. 5), each of the mount ribs 39 extends from a position immediately close to the distal end 35 (distal end face) of the mount 36 toward the proximal end of the mount 36. Since each of the first casing ribs 25a and the second casing ribs 25b extends to the proximal end (the opening 214) of the casing 21, and each of the mount ribs 39 extends from a position immediately close to the distal end 35 (distal end face) of the mount 36, when the puncture tool 2 is started to be inserted into the puncture device 10, immediately each of the casing ribs 25a or 25b enters between one of six pairs of the mount ribs 39. Accordingly, the puncture tool 2 is limited against torsional movement, and the puncture tool 2 can quickly be corrected in attitude.

As shown in FIG. 1, each of the first casing ribs 25a and the second casing ribs 25b has a proximal end edge portion 252 on the proximal end thereof, whose height and width are both progressively reduced toward the proximal end. As shown in FIG. 4, each of the mount ribs 39 has a distal end edge portion 391 on the distal end portion thereof, whose height and width are both progressively reduced toward the distal end. The proximal end edge portions 252 and the distal end edge portions 391 provide a better guiding function, thus enabling the puncture tool 2 to be easily inserted into the puncture device 10. Even if the proximal end edge portions 252 and the distal end edge portions 391 impinge upon each other (i.e., hit each other) when the puncture tool 2 is inserted into the puncture device 10, the proximal end edge portions 252 and the distal end edge portions 391 slide against each other and move in circumferential directions, thereby causing the puncture tool 2 to rotate about the central axis O1. Therefore, one casing rib 25a or 25b can enter between two mount ribs 39 of each of the adjacent six pairs of the mount ribs 39, and hence the ribs (e.g., the mount ribs 39 and the casing ribs 25a) are prevented from coming into fitting engagement with each other, so as to reliably correct the puncture tool 2 in attitude.

Although the puncture set according to the present invention has been described above with reference to the illustrated embodiment, the present invention is not limited to the illustrated embodiment, but rather, various components of the puncture set may be replaced with other desired components having similar functions. Furthermore, desired components may be added.

The puncture set is arranged such that, during the process of mounting the puncture tool in the puncture device, the crest of each first casing rib is abutted against the inner circumferential surface of the mount. However, the puncture set is not limited to such a structure, and may be arranged such that the crest of each mount rib is abutted against the outer circumferential surface of the casing, for example.

In the aforementioned puncture set (puncture tool), the total number of ribs of the mount is greater than the total number of ribs of the casing. However, the total number of ribs of the mount or the casing is not limited. The total number of ribs may be equal to or smaller than the total number of ribs of the casing, for example.

Each mount rib extends from a position immediately close to the distal end of the mount toward the proximal end. However, the mount ribs are not limited to such a structure, and may also extend from the distal end of the mount toward the proximal end, for example.

INDUSTRIAL APPLICABILITY

The puncture set according to the present invention comprises a puncture needle unit having a puncture needle including a needle body having a sharp needle point at a distal end thereof and a needle hub fixed to a proximal end of the needle body, and a tubular casing housing the puncture needle longitudinally movably therein and having an opening through which the needle point can project, and a puncture device having a housing, a ring-shaped mount disposed on a distal end portion of the housing for holding the casing removably mounted therein, and a plunger housed in the housing and having a coupling for being coupled to the needle hub in a mounted state in which the casing is mounted in the mount, wherein the casing has a plurality of casing protrusions that project on an outer circumferential surface thereof and which are disposed circumferentially along the outer circumferential surface, and the mount having a plurality of mount protrusions that project on an inner circumferential surface thereof and which are disposed circumferentially along the inner circumferential surface, at least one of the mount protrusions being positioned between an adjacent two of the casing protrusions in the mounted state. When the puncture needle unit is mounted in the puncture device, a space (gap) is formed between the outer circumferential surface of the casing of the puncture needle unit and the inner circumferential surface of the mount of the puncture device. Within this space, each of the casing protrusions enters between an adjacent two of the mount protrusions in the circumferential direction of the mount, thereby creating areas of reduced gap length. The puncture needle unit is thus limited against radial movement, thereby allowing the puncture needle of the puncture needle unit and the plunger of the puncture device to be reliably coupled to each other in a mounted state. Consequently, the puncture set according to the present invention has industrial applicability.

The invention claimed is:

1. A puncture set comprising:
a puncture needle unit having a puncture needle including a needle body having a sharp needle point at a distal end thereof and a needle hub fixed to a proximal end of the needle body, and a tubular casing housing the puncture needle longitudinally movably therein and having an opening through which the needle point can project; and
a puncture device having a housing, a ring-shaped mount disposed on a distal end portion of the housing for holding the casing removably mounted therein, and a plunger housed in the housing and having a coupling for being coupled to the needle hub in a mounted state in which the casing is mounted in the mount,
wherein the casing has a plurality of casing protrusions that project on an outer circumferential surface thereof and which are disposed circumferentially along the outer circumferential surface, and the mount has a plurality of mount protrusions that project on an inner circumferential surface thereof and which are disposed circumferentially along the inner circumferential surface, at least one of the mount protrusions being positioned between an adjacent two of the casing protrusions in the mounted state,
wherein a number of the mount protrusions is greater than a number of the casing protrusions;
wherein each of the mount protrusions comprises a ridge that extends along a central axis of the mount and each of the mount protrusions extends from a distal end face of the mount, or from a position immediately close to the distal end face; and
wherein each of the casing protrusions comprises a ridge that extends along a central axis of the casing and each of the casing protrusions reaches a proximal end surface of the casing.

2. A puncture set according to claim 1, wherein the needle hub includes a hollow cylindrical portion disposed on a proximal end portion thereof concentrically with the casing; and the coupling comprises a hollow cylindrical region disposed concentrically with the mount and fitted over the hollow cylindrical portion in the mounted state.

3. A puncture set according to claim 2, wherein, during a process of reaching the mounted state, the puncture needle unit is corrected to bring a central axis of the hollow cylindrical portion into alignment with a central axis of the coupling when at least one of the mount protrusions is positioned between an adjacent two of the casing protrusions.

4. A puncture set according to claim 1, wherein, during a process of reaching the mounted state, the mount protrusions have crests abutted against the outer circumferential surface of the casing, or the casing protrusions have crests abutted against the inner circumferential surface of the mount.

5. A puncture set according to claim 1, wherein the mount protrusions are disposed at equal angular intervals about a central axis of the mount.

6. A puncture set according to claim 1, wherein each of the mount protrusions has, on a distal end portion thereof, a height, a width, or a height and a width that are progressively reduced toward the distal end.

7. A puncture set according to claim 1, wherein the casing protrusions are disposed at equal angular intervals about a central axis of the casing.

8. A puncture set according to claim 1, wherein adjacent ones of the casing protrusions have different heights.

9. A puncture set according to claim 1, wherein each of the casing protrusions has, on a proximal end thereof, a height, a width, or a height and a width that are progressively reduced toward the proximal end.

10. A puncture set according to claim 1, wherein the puncture device has an ejection mechanism housed in the mount, and having an ejection member that covers the plunger.

11. A puncture set according to claim 10, wherein the ejection member has a plurality of ejection protrusions projecting on an outer circumferential surface thereof and disposed circumferentially along the outer circumferential surface, wherein, when at least one of the mount protrusions is positioned between an adjacent two of the ejection protrusions, the ejection member performs a guiding function to prevent the coupling from bending radially with respect to a central axis thereof and to fix the coupling and the plunger along the central axis.

12. A puncture set according to claim 1, wherein the needle hub comprises a hollow cylindrical portion having an outside diameter that progressively increases from a proximal end toward a distal end thereof.

* * * * *